United States Patent [19]

Suzukamo et al.

[11] Patent Number: 4,992,612

[45] Date of Patent: Feb. 12, 1991

[54] SOLID BASE, PROCESS FOR PRODUCING THE SAME AND PROCESS OF PREPARING INTERNAL OLEFINS

[75] Inventors: Gohfu Suzukamo, Ibaraki; Masami Fukao, Shiga, both of Japan

[73] Assignee: Sumitomo Chemical Company, Limited, Osaka, Japan

[21] Appl. No.: 391,243

[22] Filed: Aug. 9, 1989

[30] Foreign Application Priority Data

Aug. 12, 1988 [JP] Japan ................................. 63-202464
Aug. 12, 1988 [JP] Japan ................................. 63-202465

[51] Int. Cl.$^5$ ............................................... C07C 5/23
[52] U.S. Cl. ................................................... 585/664
[58] Field of Search ........................................ 585/664

[56] References Cited

U.S. PATENT DOCUMENTS

| | | |
|---|---|---|
| 3,432,572 | 3/1969 | Tazuma et al. . |
| 3,808,152 | 4/1974 | Nagase et al. . |
| 3,897,509 | 7/1975 | Nagase et al. . |
| 3,928,485 | 12/1975 | Nagase et al. . |
| 4,205,192 | 5/1980 | Harada . |
| 4,711,873 | 12/1987 | Suzukamo et al. . |

FOREIGN PATENT DOCUMENTS

| | | |
|---|---|---|
| 0025641 | 3/1981 | European Pat. Off. . |
| 0211448 | 2/1987 | European Pat. Off. . |
| 0230025 | 7/1987 | European Pat. Off. . |
| 0234498 | 9/1987 | European Pat. Off. . |
| 0279397 | 8/1988 | European Pat. Off. . |
| 60-94925 | 5/1985 | Japan . |
| 60-251933 | 12/1985 | Japan . |
| 62-81334 | 4/1987 | Japan . |
| 1310900 | 3/1973 | United Kingdom . |

*Primary Examiner*—Curtis R. Davis
*Attorney, Agent, or Firm*—Birch, Stewart, Kolasch & Birch

[57] ABSTRACT

A solid base obtainable by heating and reacting an alkaline earth metal compound with alumina at a temperature of from 300° to 600° C. and then heating and reacting the reaction product with at least one material selected from the group consisting of alkali metals and hydrides of alkali metals in an inert gas atmosphere at a temperature of from 200° to 450° C., which can catalyze various reaction, for example, isomerization of an olefinic double bond.

15 Claims, No Drawings

SOLID BASE, PROCESS FOR PRODUCING THE SAME AND PROCESS OF PREPARING INTERNAL OLEFINS

BACKGROUND OF THE INVENTION

1. Field of the Invention

The present invention relates to a solid base, a process for producing said solid base and a process for preparing an internal olefin in the presence of said solid base. More particularly, the present invention relates to a solid base obtainable by heating alumina, an alkaline earth metal compound and an alkali metal or its hydride at a specific temperature, a process for producing said solid base and a process for preparing an internal olefin by isomerizing an olefin in the presence of said solid base.

2. Description of the Related Art

Solid bases are technically important catalysts and used to catalyze isomerization of olefins, hydrogenation or dehydrogenation.

As such solid base, is known a solid base comprising an alkali metal supported on an alkaline earth metal oxide or a carrier consisting of an alkaline earth metal oxide and an alkali metal hydroxide (cf. Japanese Patent Kokai Publication Nos. 94925/1985 and 81334/1987). However, such the solid base comprising the alkaline earth metal oxide tends to agglomerate during its production so that its handleability is poor, and its catalytic performance is not sufficient.

Further, a solid base comprising an alkali metal hydride supported on a carrier such as alumina is known (cf. Japanese Patent Kokai Publication Nos. 121753/1978 and 134736/1984). Since such solid base comprising the alkali metal hydride can act as a catalyst in the presence of an auxiliary agent such as ammonia or hydrazine, it has some drawbacks such that a purification apparatus for separating and removing the agent is required and that the catalytic reaction is troublesome due to the use of auxiliary agent.

SUMMARY OF THE INVENTION

One object of the present invention is to provide a solid base which has high catalytic activity, does not agglomerate in the preparation, and is easy to handle.

Another object of the present invention is to provide a process for producing such novel solid base.

A further object of the present invention is to provide a process for preparing an internal olefin in the presence of such novel solid base.

These and other objects are accomplished by a solid base obtainable by heating and reacting an alkaline earth metal compound with alumina at a temperature of from 300° to 600° C. and then heating and reacting the reaction product with at least one material selected from the group consisting of alkali metals and hydrides of alkali metals in an inert gas atmosphere at a temperature of from 200° to 450° C.

DETAILED DESCRIPTION OF THE INVENTION

As alumina, preferred is alumina having a relatively large surface area such as γ-alumina, χ-alumina, ρ-alumina and η-alumina. A particle size of alumina is preferably from 50 to 400 mesh in view of handling of alumina and activity of the resulting solid base.

Examples of the alkaline earth metal compound are oxides, hydroxides, alkoxides and salts with organic or inorganic acids of elements of Group II of the Periodic Table. Examples of the alkoxides are methoxide, ethoxide, etc. Examples of the organic or inorganic salts are carbonate, hydroxide, formate, acetete, propionate, etc. Preferably, the oxides and hydroxides of magnesium, calcium, barium and strontium are used.

Such the compound is used in the form of a solution or a dispersion in which the compound is finely dispersed. Examples of a liquid medium are water and organic solvent such as alcohol, acetic acid, etc.

To react the alkaline earth metal compound with alumina, the solution or dispersion of said compound is poured to alumina at the specific temperature while stirring, or alumina is immersed in the solution or dispersion to have the compound carried on alumina and then heated to react the compound with alumina. Alternatively, when the alkaline earth metal compound melts at the specific temperature at which alumina and the compound are reacted, the compound and alumina as such are heated and reacted.

The alkali metal is selected from metals of Group I of the Periodic Table, and preferably lithium, sodium and potassium. Examples of the alkali metal hydride are lithium hydride, sodium hydride and potassium hydride. Among them, sodium, potassium, sodium hydride and potassium hydride are preferred. Mixtures of two or more of the alkali metals and their hydrides may be used.

The amounts of the alkaline earth metal compound and of the alkali metal or its hydride are 5 to 100% by weight and 2 to 15% by weight, respectively based on the weight of alumina.

The preparation temperatures in the production of the solid base are very important. In particular, the temperature at which the alkali metal or its hydride is reacted greatly influences the catalytic performance of the solid base.

Alumina and the alkaline earth metal compound are reacted at a temperature of from 300° to 600° C., preferably from 300° to 550° C. The alkali metal or its hydride is reacted at a temperature of from 200° to 450° C., preferably from 250° to 400° C., more preferably from 280° to 350° C. When the solid base is produced under such temperature conditions, it has very high catalytic activity so that a small amount of the solid base can catalyze desired reactions effectively.

The reaction of the alkali metal or its hydride with the reaction product of alumina and the alkaline earth metal compound is usually carried out in an atmosphere of inert gas such as nitrogen, helium, argon and the like.

The reaction time varies with other reaction conditions such as reaction temperatures. The reaction time for reacting the alkaline earth metal compound with alumina is from 0.5 to 10 hours, and the reaction time for reacting the alkali metal or its hydride is from 5 to 300 minutes.

The thus produced solid base of the present invention may comprise a new active species formed from alumina, the alkaline earth metal compound and the alkali metal or its hydride, and can catalyze the desired reaction without any auxiliary agent such as ammonia or hydrazine. The solid base of the present invention does not agglomerate and has good fluidity so that its handleability during production and in use is good. Therefore, the solid base of the present invention can be used as the catalyst for various reactions in the industrial scale.

For example, the solid base of the present invention can be used for catalyzing isomerization of olefins and various condensation reactions which are catalyzed with bases. Among such reactions, the solid base of the present invention has good catalytic activity on the isomerization of olefins. For example, isomerization of an olefin to an internal olefin, particularly isomerization of an alkenyl substituted bridged-cyclic compound to an alkylidene bridged-ring compound proceeds only by contacting a starting olefin with the solid base of the present invention.

Now the preparation of internal olefins by the use of the solid base of the present invention is explained.

Examples of olefins to be isomerized are terminal olefins such as unsaturated aliphatic compounds (e.g. 1-butene, 1-pentene, 1-hexene, 1-heptene, 1-nonene, 1-decene, 2-methyl-1-butene, 3-methyl-1-butene, 4-methyl-1-pentene, 3-methyl-1-pentene, 2-methyl-1-pentene, 2,3-dimethyl-1-butene, etc.), aromatic compounds (e.g. allylbenzene, allyltoluene, etc.), bridged ring compounds (2-isopropenylnorbornene, 5-isopropenyl-2-norbornene, 5-vinyl-2-norbornene, 6-methyl-5-vinylnorbornene, etc.), cyclic compounds (e.g. methylenecyclopentane, methylenecyclohexane, etc.), diolefins (e.g. 1,4-pentadiene, 1,5-hexadiene, 2,5-dimethyl-1,4-hexadiene, 2,5-dimethyl-1,5-hexadiene, etc.), and compounds having an internal double bond which can be isomerized to a more stable position (e.g. 4-methyl-2-pentene, 5-(2-propenyl)-2-norbornene, etc.).

In the preparation of internal olefin, the amount of solid base to be used is from 1/3,000 to 1/50, preferably from 1/2,000 to 1/100 part by weight per part of the raw material olefin.

It is not necessarily required to heat the reaction system since isomerization proceeds at room temperature, although the reaction system may be heated. Usually, the isomerization temperature is from $-30°$ to $+120°$ C., preferably from $-10°$ to $+100°$ C.

Optionally, an inert solvent may be used. Examples of the inert solvent are hydrocarbons such as pentane, hexane, heptane, dodecane, cyclohexane, benzene, toluene, etc.

The isomerization is carried out batch wise or continuously. Preferably, the raw material olefin is pretreated with a drying agent such as alumina and molecular sieves. For assuring the complete and safe proceeding of the reaction, the isomerization may be carried out in an atmosphere of an inert gas such as nitrogen, helium and argon.

The isomerization product is usually analyzed by such method as gas chromatography and isolated from the catalyst by a conventional manner such as filtration or decantation.

By the above reaction, the internal olefins in which the unsaturated bond is isomerized to the more stable position are prepared. According to the present invention, a small amount of the solid base can effectively isomerize the olefins in the absence of the auxiliary agent such as ammonia or hydrazine to give the internal olefins in high yields without the formation of by-products such as polymerized materials. Further, the solid base of the present invention can promote the reactions without any danger such as ignition. Then, the process of the present invention is a technically advantageous process.

Practically and presently preferred embodiments of the present invention will be illustrated by following examples.

EXAMPLE 1

(1.1) Light magnesia (10 g) was ground in a mortar and suspended in water (400 g). To the suspension, γ-alumina containing 2.2% of water (100 g) was added while stirring. Then, water was evaporated off at 60° C. under reduced pressure to obtain a granular material (119.5 g).

(1.2) The granular material (25 g) obtained in (1.1) was stirred in a nitrogen stream at 510° C. for 2 hours. After cooling to 300° C., metal sodium (1.2 g) was added thereto and stirred at the same temperature for 30 minutes followed by cooling to room temperature to obtain an off-white solid base (21.4 g).

COMPARATIVE EXAMPLE 1

The same magnesia as used in Example 1 (15.2 g) was stirred in a nitrogen stream at 510° C. for 2 hours. After cooling to 300° C., metal sodium (0.73 g) was added to the sintered magnesia and stirred at the same temperature for 30 minutes although the uniform stirring was difficult. Then, the mixture was cooled to room temperature to obtain a gray solid base.

EXAMPLES 2-3 AND COMPARATIVE EXAMPLES 2-3

In the same manner as in Example 1 but changing the stirring temperature in the step (1.2) from 300° C. to 170° C., 250° C., 400° C. or 510° C., a solid base shown in Table 1 was obtained.

EXAMPLE 4

(4.1) In the same manner as in the step 1.1 of Example 1 but using magnesium hydroxide (15 g) in place of magnesia, a granular material (115.2 g) was obtained.

(4.2) The granular material (25 g) obtained in (4.1) was stirred in a nitrogen stream at 510° C. for 3 hours. After cooling to 360° C., sodium hydride (1.3 g) was added thereto and stirred at the same temperature for 30 minutes followed by cooling to room temperature to obtain a solid base shown in Table 1.

EXAMPLE 5

The granular material obtained in the step (1.1) of Example 1 (25 g) was stirred in a nitrogen stream at 510° C. for 3 hours. After cooling to 310° C., potassium hydride (1.4 g) was added thereto and stirred at the same temperature for 30 minutes followed by cooling to room temperature to obtain a solid base shown in Table 1.

EXAMPLE 6

(6.1) In the same manner as in the step 1.1 of Example 1 but using calcium oxide (12.1 g) in place of magnesia, a granular material (113 g) was obtained.

(6.2) The granular material (25 g) obtained in (6.1) was stirred in a nitrogen stream at 510° C. for 2 hours. After cooling to 310° C., metal potassium (1.4 g) was added thereto and stirred at the same temperature for 30 minutes followed by cooling to room temperature to obtain a solid base shown in Table 1.

TABLE 1

| Example No. | Alkaline earth metal compound | Alkali metal or its hydride (Reaction temp.) | Solid base Color | Yield (g) |
|---|---|---|---|---|
| 2 | Magnesia | Na (250° C.) | Gray | 21.4 |

TABLE 1-continued

| Example No. | Alkaline earth metal compound | Alkali metal or its hydride (Reaction temp.) | Solid base Color | Yield (g) |
|---|---|---|---|---|
| 3 | Magnesia | Na (400° C.) | Off-white | 21.4 |
| 4 | MgOH | NaH (360° C.) | Off-white | 21.5 |
| 5 | Magnesia | KH (310° C.) | Grayish blue | 21.8 |
| 6 | CaO | K (310° C.) | Grayish blue | 21.8 |
| Comp. 2 | Magnesia | Na (170° C.) | Gray | 21.5 |
| Comp. 3 | Magnesia | Na (510° C.) | Off-white | 21.2 |

EXAMPLE 7

To a 200 ml flask in nitrogen atmosphere, the solid base obtained in Example 1 (0.20 g) and 5-vinyl-2-norbornene (hereinafter referred to as "VNB") (74 g) were added and stirred at a temperature of 15°-20° C. for 8 hours.

Then, the catalyst was filtered off to obtain a reaction mixture (73.3 g). Gas chromatographic analysis of the mixture revealed that 99.4% of 5-ethylidene-2-norbornene (hereinafter referred to as "ENB") and 0.5% of VNB were contained in the product.

EXAMPLES 8-12 AND COMPARATIVE EXAMPLES 4-6

In the same manner as in Example 7 but using each of the solid bases obtained in Examples 2-6 and Comparative Examples 1-3 and carrying out the isomerization under conditions shown in Table 2, VNB was isomerized to ENB. The results are shown in Table 2.

TABLE 2

| Example No. | Solid base (g) | Amount of VNB | Reaction conditions Temp. (°C.) | Time (hrs) | Reaction results VNB (%) | ENB (%) |
|---|---|---|---|---|---|---|
| 8 | Example 2 (0.25) | 50.9 | 15-20 | 8 | 0.4 | 99.5 |
| 9 | Example 3 (0.24) | 37 | 15-20 | 8 | 0.4 | 99.5 |
| 10 | Example 4 (0.25) | 86.7 | 15-20 | 8 | 0.7 | 99.2 |
| 11 | Example 5 (0.18) | 81.9 | 15-20 | 8 | 0.2 | 99.0 |
| 12 | Example 6 (0.3) | 75.6 | 15-20 | 8 | 0.3 | 99.1 |
| Comp. 4 | Comp. Ex. 1 (0.2) | 20 | 15-20 | 24 | 16.4 | 83.6 |
| Comp. 5 | Comp. Ex. 2 (0.3) | 15 | 15-20 | 24 | 3 | 96.9 |
| Comp. 6 | Comp. Ex. 3 (0.3) | 24 | 15-20 | 24 | 0.6 | 99.3 |

EXAMPLE 13

To a 100 ml flask in nitrogen atmosphere, the solid base obtained in Example 1 (0.2 g) and 4-methyl-1-pentene (30 g) were added and stirred at a temperature of 15°-20° C. for 16 hours. Then, the catalyst was filtered off to obtain a reaction mixture. Gas chromatographic analysis of the mixture revealed that 0.4% of 4-methyl-1-pentene, 9.1% of 4-methyl-2-pentene and 90.3% of 2-methyl-2-pentene were contained in the product.

EXAMPLE 14

To a 100 ml flask in nitrogen atmosphere, the solid base obtained in Example 1 (0.22 g) and 2,3-dimethyl-1-butene (99.4% of 2,3-dimethyl-1-butene and 0.6% of tetramethylethylene) (41 g) were added and stirred at a temperature of 15°-20° C. for 16 hours. Then, the catalyst was filtered off to obtain a reaction mixture. Gas chromatographic analysis of the mixture revealed that 7.3% of 2,3-dimethyl-1-butene and 92.7% of tetramethylethylene were contained in the product.

EXAMPLE 15

To an aqueous solution of barium hydroxide octahydrate (4.6 g), γ-alumina (26.5 g) was added and concentrated to dryness under reduced pressure while stirring.

Then, the product was stirred at 500° C. in nitrogen atmosphere for 1.5 hours and cooled to 290° C. To the product, metal potassium (2 g) was added and the mixture was stirred at the same temperature for 0.2 hour followed by cooling to room temperature to obtain a bluish gray powder.

EXAMPLE 16

To a 200 ml flask in nitrogen atmosphere, the solid base obtained in Example 15 (0.24 g) and VNB (121.6 g) were added and stirred at a temperature of 20°-25° C. for 3 hours. Then, the catalyst was filtered off to obtain a reaction mixture (120.9 g). Gas chromatographic analysis of the mixture revealed that 99.1% of ENB and 0.6% of VNB were contained in the product.

EXAMPLE 17

γ-Alumina (20 g) and magnesium acetate tetrahydrate (10.6 g) were stirred in an air stream at 470° C. for 4 hours. After cooling the mixture to 300° C. in a nitrogen stream, metal potassium (2.52 g) was added and stirred at the same temperature for 0.2 hour followed by cooling to room temperature to obtain a bluish gray material.

EXAMPLE 18

To a 200 ml flask in nitrogen atmosphere, the solid base obtained in Example 17 (0.25 g) and VNB (122.9 g) were added and stirred at a temperature of 20°-25° C. for 2 hours. Then, the catalyst was filtered off to obtain a reaction mixture (122.1 g). Gas chromatographic analysis of the mixture revealed that 99.3% of ENB and 0.4% of VNB were contained in the product.

What is claimed is:

1. A process for preparing an internal olefin comprising isomerizing an olefin in the presence of a solid base obtainable by heating and reacting an alkaline earth metal compound with alumina at a temperature of from 300° to 600° C. and then heating and reacting the resulting product with at least one material selected from the group consisting of alkali metals and hydrides of alkali metals in an inert gas atmosphere at a temperature of from 200° to 450° C.

2. The process according to claim 1, wherein alumina is selected from the group consisting of γ-alumina, χ-alumina, ρ-alumina and η-alumina.

3. The process according to claim 1, wherein alumina has a particle size of 50 to 400 mesh.

4. The process according to claim 1, wherein the alkaline earth metal compound is at least one selected from the group consisting of oxides, hydroxides, alkoxides, organic acid salts and inorganic acid salts of the elements of Group II of the Periodic Table.

5. The process according to claim 1, wherein the alkaline earth metal compound is at least one selected from the group consisting of oxides, hydroxides and organic acid salts of magnesium, calcium, barium and strontium.

6. The process according to claim 1, wherein the amount of the alkaline earth metal compound is 5 to 100% by weight based on the weight of alumina.

7. The process according to claim 1, wherein the alkaline earth metal compound is reacted with alumina at a temperature of from 300° to 550° C.

8. The process according to claim 1, wherein an alkali metal is reacted with the reaction product of alumina and the alkaline earth metal compound.

9. The process according to claim 8, wherein the alkali metal is at least one selected from the group consisting of lithium, sodium and potassium.

10. The process according to claim 1, wherein an alkali metal hydride is reacted with the reaction product of alumina and the alkaline earth metal compound.

11. The process according to claim 10, wherein the alkali metal hydride is at least one selected from the group consisting of lithium hydride, sodium hydride and potassium hydride.

12. The process according to claim 1, wherein the amount of the alkali metal or its hydride is 2 to 15% by weight based on the weight of alumina.

13. The process according to claim 1, wherein the alkali metal or its hydride is reacted with the reaction product of alumina and the alkaline earth metal compound at a temperature of from 250° to 400° C.

14. The process according to claim 1, wherein the amount of solid base is from 1/3,000 to 1/50 part by weight per part of the raw material olefin.

15. The process according to claim 1, wherein the isomerization temperature is from −30° to +120° C.

* * * * *